United States Patent
Chua et al.

(10) Patent No.: US 10,357,371 B2
(45) Date of Patent: Jul. 23, 2019

(54) HIP PROSTHESIS DEVICES

(71) Applicant: SINGAPORE HEALTH SERVICES PTE. LTD., Singapore (SG)

(72) Inventors: Kenon Chua, Singapore (SG); Andy Khye Soon Yew, Singapore (SG); Ngal Nung Lo, Singapore (SG)

(73) Assignee: SINGAPORE HEALTH SERVICES PTE. LTD., Singapore (SG)

( * ) Notice: Subject to any disclaimer, the term of this patent is extended or adjusted under 35 U.S.C. 154(b) by 61 days.

(21) Appl. No.: 15/513,580

(22) PCT Filed: Sep. 23, 2015

(86) PCT No.: PCT/SG2015/050340
§ 371 (c)(1),
(2) Date: Mar. 23, 2017

(87) PCT Pub. No.: WO2016/048244
PCT Pub. Date: Mar. 31, 2016

(65) Prior Publication Data
US 2017/0296347 A1 Oct. 19, 2017

Related U.S. Application Data

(60) Provisional application No. 62/054,405, filed on Sep. 24, 2014.

(51) Int. Cl.
*A61F 2/32* (2006.01)
*A61F 2/36* (2006.01)
(Continued)

(52) U.S. Cl.
CPC ............ *A61F 2/3662* (2013.01); *A61B 17/74* (2013.01); *A61F 2/30744* (2013.01);
(Continued)

(58) Field of Classification Search
CPC .. A61F 2002/30538; A61F 2002/30601; A61F 2/3859; A61F 2002/30828;
(Continued)

(56) References Cited

U.S. PATENT DOCUMENTS 5,389,107 A * 2/1995 Nassar ................. A61B 17/746
623/23.17
6,248,132 B1 6/2001 Harris
(Continued)

FOREIGN PATENT DOCUMENTS

EP 1872744 A1 1/2008

*Primary Examiner* — Ann Schillinger
(74) *Attorney, Agent, or Firm* — Hultquist, PLLC; Steven J. Hultquist

(57) ABSTRACT

A hip prosthesis device including a femoral stem, the femoral stem including an elongate stem sleeve having a blind hole extending in a longitudinal direction and a hole opening at an upper frontal end of the stem sleeve; a stem core having an elongate stem shaft inserted in the blind hole and slidable in the longitudinal direction, a neck having a lower neck portion and an upper neck portion, a lower end of a lower neck portion attached to an upper end of the stem shaft, the upper neck portion attachable to a femoral head; a shock absorber mechanism operatively provided between the stem shaft and the stem sleeve to act against a downwardly directed longitudinal sliding motion of the stem shaft relative to the stem sleeve; and a closure cap positioned to close the hole opening with a through hole which the neck extends with its lower neck portion.

18 Claims, 7 Drawing Sheets

(51) Int. Cl.
*A61F 2/30* (2006.01)
*A61B 17/74* (2006.01)

(52) U.S. Cl.
CPC ............. *A61F 2002/3037* (2013.01); *A61F 2002/30156* (2013.01); *A61F 2002/30365* (2013.01); *A61F 2002/30558* (2013.01); *A61F 2002/30566* (2013.01); *A61F 2002/30568* (2013.01); *A61F 2002/30589* (2013.01); *A61F 2002/30593* (2013.01); *A61F 2002/30601* (2013.01); *A61F 2002/30733* (2013.01); *A61F 2002/365* (2013.01); *A61F 2002/3652* (2013.01); *A61F 2002/3674* (2013.01); *A61F 2002/3692* (2013.01); *A61F 2002/3694* (2013.01); *A61F 2310/00389* (2013.01)

(58) Field of Classification Search
CPC ...... A61F 2002/4475; A61F 2002/4666; A61F 2/32; A61F 2/30; A61F 2/36; A61F 2/3601; A61F 2/4014
See application file for complete search history.

(56) References Cited

U.S. PATENT DOCUMENTS

| | | |
|---|---|---|
| 6,336,941 B1 | 1/2002 | Subba Rao et al. |
| 2001/0051831 A1* | 12/2001 | Subba Rao ........... A61F 2/3609 623/22.42 |
| 2003/0060891 A1 | 3/2003 | Shah |
| 2010/0331984 A1 | 12/2010 | Barsoum et al. |

\* cited by examiner

HIP PROSTHESIS DEVICES

CROSS-REFERENCE TO RELATED APPLICATIONS

The present application is a U.S. national phase under the provisions of 35 U.S.C. § 371 of International Patent Application No. PCT/SG2015/050340 filed Sep. 23, 2015, which in turn claims the benefit of U.S. Provisional Patent Application No. 62/054,405 filed on Sep. 24, 2014. The disclosures of such international patent application and U.S. provisional patent application are hereby incorporated herein by reference in their respective entireties, for all purposes.

TECHNICAL FIELD

Embodiments generally relate to hip prosthesis devices.

BACKGROUND

Total hip replacement (THR) is currently the gold standard treatment in the management of severe hip osteoarthritis as well as other end-stage hip conditions. In THR, the femoral head and acetabulum are respectively replaced with an artificial femoral stem and acetabular cup. At the proximal end of the femoral stem is a neck that terminates in a spherical ball and is generally referred to as the femoral head. The spherical geometry of the artificial femoral head enables it to freely articulate with the patient's acetabulum or a prosthetic acetabular cup fixed into the patient's acetabulum. To facilitate fixation of the femoral stem into the femur, it typically includes a shank portion (in other words a stem) that is inserted into the medullary canal of the femur. Fixation can be via the use of bone cement or press-fitted with treated surface that promotes bone ingrowth or ongrowth. THR prosthesis are currently available as either a two to three component system. In the three component system, it includes a femoral stem shank, a femoral head and an acetabular cup.

The purpose of THR is to replace the diseased hip joint with THR implants that can simulate the hip joint so as to enable load bearing and ambulation. In the course of load bearing and different ambulation activities, the replacement hip is subjected to repeated large impact forces, ranging from 2 to 8 times the body weight. Over time, such impactful forces may lead to loosening of the hip implant, including the femoral stem component. The impact forces may result in micromotion at the cement implant interface for cemented femoral stem. For press-fit bone ingrowth stem, any deficiency in bone ingrowth together with such constant impact forces may also lead to micromotion at the bone implant interface. This micromotion may result in femoral stem mechanical loosening. As a result of the above, revision surgery may be necessary. Current hip prosthesis has little intrinsic ability to reduce this impact force during axial loading. Further, wear particles generated from the abrasive forces acting on the prosthetic head in relation to the prosthetic acetabular may also contribute to loosening of the implant by osteolysis. When osteolysis takes place, the supporting bone structure fixed to the implant may be resorbed and hence biological loosening may occur.

U.S. Pat. Nos. 6,248,132, 5,389,107 and 6,336,941 attempt to address the undesirable side effects of large impact force experienced at the artificial hip joint.

In U.S. Pat. No. 6,248,132, to avoid micromotion from the large impact force, the acetabular cup was allowed to be displaced in its local axial direction during the load bearing via wave spring washers. Its femoral stem was inserted into a L-shaped shield fixed into the femur.

In U.S. Pat. Nos. 5,389,107 and 6,336,941, a force damping mechanism via springs was provided at the artificial femoral head. The shock absorption ability of the artificial hip joints in U.S. Pat. Nos. 6,248,132, 5,389,107 and 6,336,941 may not be effective. This is because these artificial hip joints are only able to displace in the local axial direction of the femoral head or the prosthetic acetabular cup. However, in the implanted artificial hip joint, the resultant joint force exerted on the prosthetic femoral head is in the superior-inferior anatomical direction and not in the local axial direction of the prosthetic femoral head or acetabular cup. Thus, the motion of the femoral stem component moves mainly in the superior-inferior anatomical direction, and not diagonally into or out of the hip joint.

In addition, it is well established in the literature that when loosening occurs in the femoral stem, it may be along the shank region and may always be in the direction of the femoral axial axis which is almost parallel to the superior-inferior anatomical direction. U.S. Pat. Nos. 5,389,107 and 6,336,941 clearly do not discuss loosening of the femoral stem along the femoral axial axis or avoiding micromotion along the femoral axial direction.

For U.S. Pat. No. 6,248,132, its femoral stem was inserted into a L-shaped shield fixed into the femur. The arrangement merely prevents the femoral stem from moving up along the L-shaped protective shield by way of a saw tooth step features. The flaw in U.S. Pat. No. 6,246,132 is that firstly, it merely stops the femoral stem from migrating upwards. In other words, it allows the femoral stem to move downwards relative to the shield, and does not allow the prosthesis to return to its original position subsequently. Such arrangement does not appear to be useful to avoid micromotion or to prevent loosening of the femoral stem along the femoral axial axis. In addition, the saw tooth step features has poor inherent longevity.

Therefore, there exists a need to address at least some of the issues identified in the existing hip prosthesis device.

SUMMARY

According to various embodiments, there is provided a hip prosthesis device including a femoral stem which is provided to be implanted within a femoral bone, the femoral stem comprising: an elongate stem sleeve having a blind hole formed therein and extending in a longitudinal direction thereof and having a hole opening at an upper frontal end of the stem sleeve; a stem core which has an elongate stem shaft inserted in the blind hole and arranged therein so as to be slidable in the longitudinal direction thereof, a neck with a lower neck portion which is fixedly attached, with a lower end thereof, to an upper end of the stem shaft, and with an upper neck portion which is fixedly attached, with a lower end thereof, to an upper end of the lower neck portion and which has an upper end, to which a femoral head is attachable; a shock absorber mechanism arranged within the stem sleeve and operatively provided between the stem shaft and the stem sleeve so as to act at least against a downwardly directed longitudinal sliding motion of the stem shaft relative to the stem sleeve; and a closure cap positioned so as to close the hole opening and having a through hole provided therethrough, through which the neck extends with its lower neck portion.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DETAILED DESCRIPTION

Embodiments described below in context of the apparatus are analogously valid for the respective methods, and vice versa. Furthermore, it will be understood that the embodiments described below may be combined, for example, a part of one embodiment may be combined with a part of another embodiment.

It should be understood that the terms "on", "over", "top", "bottom", "down", "side", "back", "left", "right", "front", "frontal", "lateral", "side", "up", "down", "upper", "lower", "upwardly", "downwardly", "inner", "outer" etc., when used in the following description are used for convenience and to aid understanding of relative positions or directions, and not intended to limit the orientation of any device, or structure or any part of any device or structure.

Figure 1:
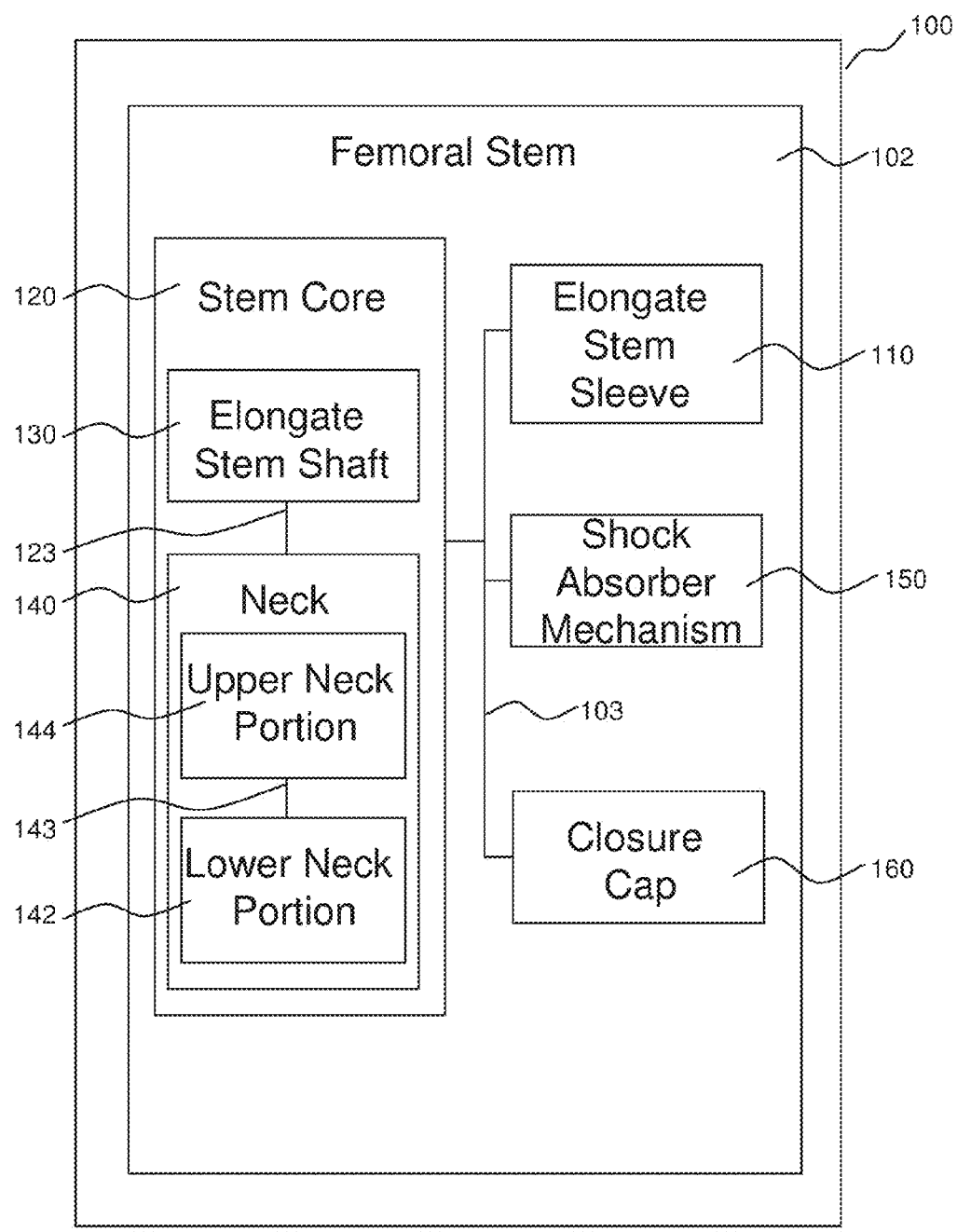
FIG. 1 shows schematic block diagram of a hip prosthesis device 100 according to various embodiments.

FIG. 1 shows schematic block diagram of a hip prosthesis device 100 according to various embodiments. The hip prosthesis device 100 may include a femoral stem 102. The femoral stem 102 may be provided to be implanted within a femoral bone. The femoral stem 102 may include an elongate stem sleeve 110. The elongate stem sleeve 110 may include a blind hole formed therein and extending in a longitudinal direction thereof. The elongate stem sleeve 110 may further include a hole opening at an upper frontal end of the stem sleeve 110. The femoral stem 102 may further include a stem core 120. The stem core 120 may include an elongate stem shaft 130 inserted in the blind hole and arranged therein so as to be slidable in the longitudinal direction thereof. The stem core 120 may include a neck 140 with a lower neck portion 142 which may be fixedly attached, with a lower end thereof, to an upper end of the stem shaft 130, and with an upper neck portion 144 which may be fixedly attached, with a lower end thereof, to an upper end of the lower neck portion 142 and which has an upper end, to which a femoral head may be attachable. Line 123 in FIG. 1 represents the connection between the stem shaft 130 and the neck 140. Line 143 in FIG. 1 represents the connection between the lower neck portion 142 and the upper neck portion 144. The femoral stem 102 may further include a shock absorber mechanism 150 arranged within the stem sleeve 110 and operatively provided between the stem shaft 130 and the stem sleeve 110 so as to act at least against a downwardly directed longitudinal sliding motion of the stem shaft 130 relative to the stem sleeve 110. The femoral stem 102 may further include a closure cap 160 positioned so as to close the hole opening and having a through hole provided therethrough, through which the neck 140 extends with its lower neck portion 142. Lines 103 in FIG. 1 represent the various relationships and the interactions between the stem sleeve 110, the stem core 120, the shock absorber mechanism 150 and the closure cap 160.

In other words, the hip prosthesis device 100 may be a prosthetic implant for hip replacement. The hip prosthetic implant may include a femoral component (in other words a femoral stem 102) that may be fitted into a femoral bone. The femoral component may include an elongated body having a tubular internal cavity (in other words a stem sleeve 110 having a blind hole). The tubular internal cavity of the elongated body may extend longitudinally from an end surface of the elongated body in without breaking through to the other end of the elongated body. The elongated body may be adapted to be implanted into a femoral bone with the exterior of the elongated body adapted to be fixedly attached to the femoral bone. The femoral component may further include an interior core assembly receivable in the tubular internal cavity of the elongated body. The interior core assembly may include a center elongated member (in other words a stem shaft 130). The center elongated member may be receivable in the tubular internal cavity of the elongated body. The center elongated member may be adapted to be slidably movable in the longitudinal direction relative to the tubular internal cavity of the elongated body. The interior core assembly may further include a link member (in other words a neck 140) which is divided into an upper link portion (in other words a upper neck portion 144) and a lower link portion (in other words a lower neck portion 142). A lower end of the lower link portion may be joined to an upper end of the center elongated member. A lower end of the upper link portion may be joined to an upper end of the lower link portion. An upper end of the upper link portion may be adapted to receive a femoral head. The femoral head may be in the form of a spherical ball. The interior core assembly may further include a damping mechanism (in other words a shock absorber mechanism 150). The damping mechanism may be arranged between the tubular internal cavity of the elongated body and the center elongated member such that a biasing force may act against a longitudinal sliding motion of the center elongated member relative to the tubular internal cavity of the elongated body. The interior core assembly may further include a stopper (in other words a closure cap 160) adapted to cover an aperture of the tubular internal cavity in the end surface of the elongated body. The stopper may be adapted to include a hole so that the link member may extend through and the upper link portion and/or part of the lower link portion may be located outside of the elongated body.

Referring back to FIG. 1, according to various embodiments, the shock absorber mechanism 150 may be operatively provided between the stem shaft 130 and the stem sleeve 110 so as to act against a downwardly directed as well as against an upwardly directed longitudinal sliding motion of the stem shaft 130 relative to the stem sleeve 110.

According to various embodiments, the shock absorber mechanism 150 may be provided as a spring mechanism, or as a damping mechanism, or as a spring and damping mechanism.

According to various embodiments, the shock absorber mechanism 150 may include a first spring device arranged between a lower end of the stem shaft 130 and a bottom of the blind hole.

According to various embodiments, the shock absorber mechanism 150 may include a second spring device arranged between the upper end of the stem shaft 130 and the closure cap 160.

According to various embodiments, the first spring device may include a first helical spring. A first longitudinal end of the first helical spring may abut against the lower end of the stem shaft 130 and an opposite second longitudinal end of the first helical spring may abut against the bottom of the blind hole.

According to various embodiments, the second spring device may include a second helical spring. A first longitudinal end of the second helical spring may abut against the upper end of the stem shaft 130 and an opposite second longitudinal end of the second helical spring may abut against the closure cap 160.

According to various embodiments, the second helical spring may be arranged on the lower neck portion 142.

According to various embodiments, the hole opening may be provided with an inner thread and the closure cap 160 may be provided with a corresponding outer thread. The closure cap 160 may be screwed into the hole opening.

According to various embodiments, the closure cap 160 may close the hole opening in a sealed manner. The closure cap 160 may be in a sliding and sealed engagement with the lower neck portion 142 extending therethrough.

According to various embodiments, the hip prosthesis device 100 may further include an artificial spherical femoral head which may be fixedly attached to the upper end of the upper neck portion 144.

According to various embodiments, the stem shaft 130 may be rotatably arranged in the blind hole so as to be rotatable about a longitudinal axis of the stem shaft 130.

According to various embodiments, the blind hole and the stem shaft 130 may have circular cross sections.

According to various embodiments, the blind hole and the stem shaft 130 may have non-circular cross sections so as to allow only a limited rotation of the stem shaft 130 in the blind hole about a longitudinal direction of the stem shaft 130 relative to the stem sleeve 110.

According to various embodiments, the stem shaft 130 may be provided with an outer coating which is of higher wear resistance in comparison to a coated surface of the stem shaft 130. The coated surface may be provided with the outer coating.

According to various embodiments, an outer diameter of the stem shaft 130 and an inner diameter of the blind hole are provided so as to provide a running fit between stem shaft 130 and blind hole.

According to various embodiments, the stem shaft 130 may be adapted to slide longitudinally in the blind hole relative to the stem sleeve 110 in a gliding manner.

According to various embodiments, the upper neck portion 144 and the lower neck portion 142 may be angled relative to each other.

According to various embodiments, an outer diameter of both the upper neck portion 144 and the lower neck portion 142 may be smaller than an outer diameter of the stem shaft 130, and wherein an inner diameter of the through hole of the closure cap 160 may be smaller than the outer diameter of the stem shaft 130.

According to various embodiments, an inner diameter of the second helical spring may be smaller than the outer diameter of the stem shaft 130 and an outer diameter of the second helical spring may be larger than an inner diameter of the through hole of the closure cap 160.

Figure 2A:
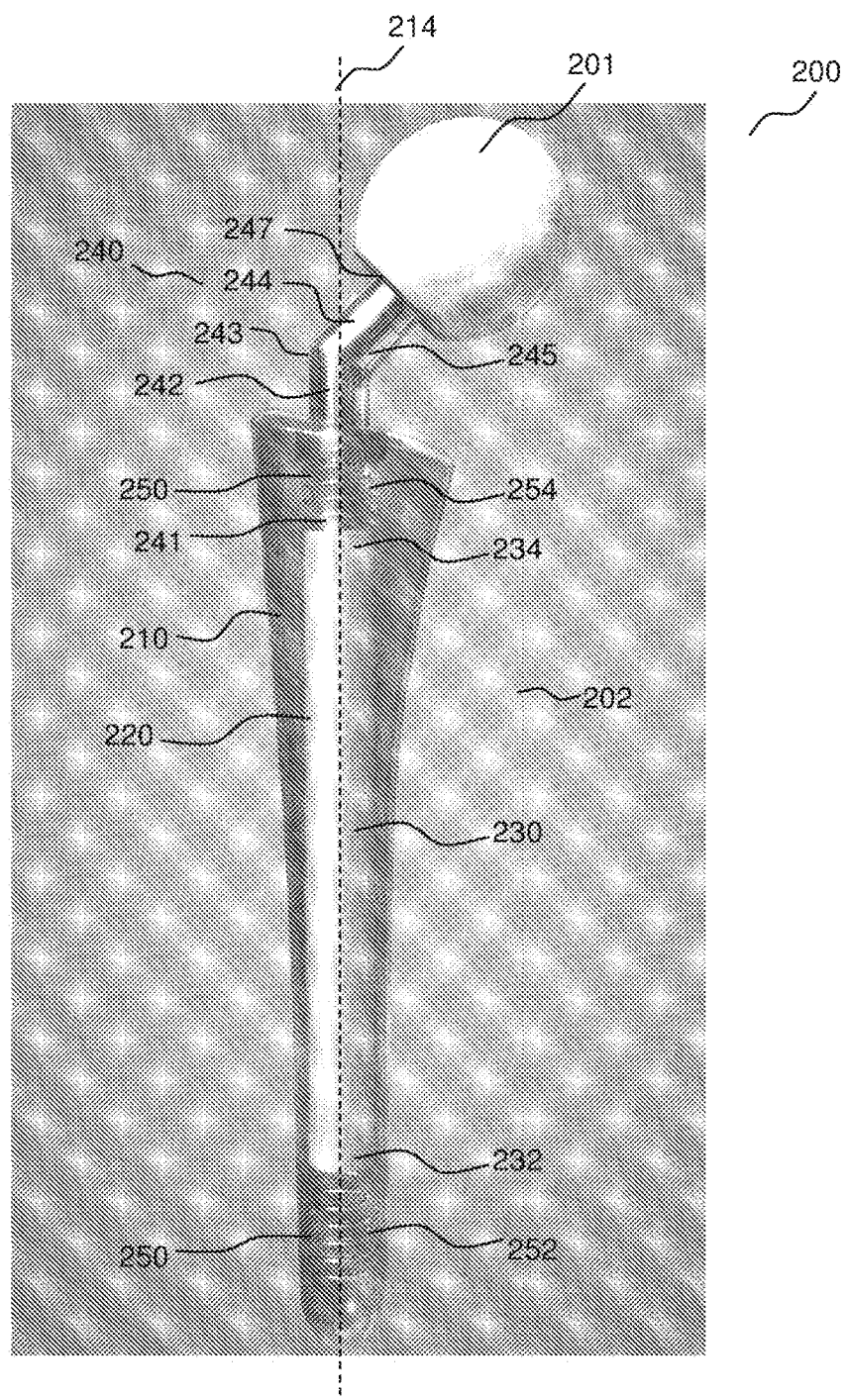
FIG. 2A shows a hip prosthesis device according to various embodiments.
Figure 2B:
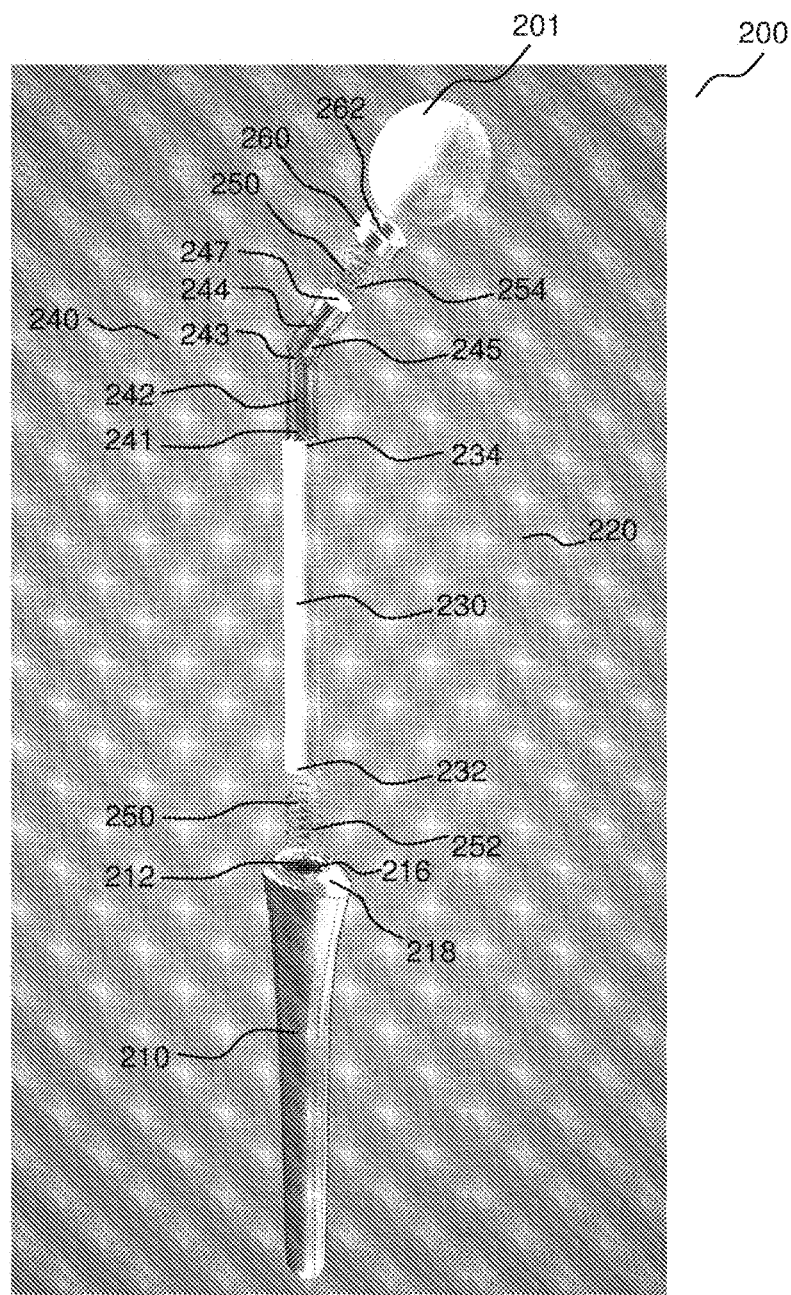
FIG. 2B shows an exploded view of the hip prosthesis device of FIG. 2A according to various embodiments.

FIG. 2A shows a hip prosthesis device (in other words a hip stem implant) 200 according to various embodiments. FIG. 2B shows an exploded view of the hip prosthesis device 200 according to various embodiments. The hip prosthesis device 200 may broadly include a femoral stem 202 and a femoral head 201 connected to the femoral stem 202. The femoral stem 202 may be adapted to be implanted within a femoral bone. The femoral stem 202 may include an elongate stem sleeve 210 having a blind hole 212 formed therein and extending in a longitudinal direction 214 thereof and having a hole opening 216 at an upper frontal end 218 of the stem sleeve. The femoral stem 202 may further include a stem core 220 having an elongate stem shaft 230 and a neck 240. The neck 240 may include a lower neck portion 242 and an upper neck portion 244. A lower end 241 of the lower neck portion 242 may be fixedly attached to an upper end 234 of the stem shaft 230. A lower end 245 of the upper neck portion 244 may be fixedly attached to an upper end 243 of the lower neck portion 242. An upper end 247 of the upper neck portion 244 may be configured such that a femoral head 201 may be attachable to the upper end 247 of the upper neck portion 244. According to various embodiments, an artificial spherical femoral head 201 may be fixedly attached to the upper end 247 of the upper neck portion 244.

The femoral stem 202 may further include a shock absorber mechanism 250 arranged within the stem sleeve 210 and operatively provided between the stem shaft 230 and the stem sleeve 210 so as to act at least against a downwardly directed longitudinal sliding motion of the stem shaft 230 relative to the stem sleeve 210. The shock absorber mechanism 250 may include two stem dampers 252, 254 attached respectively to the lower neck portion 242 and lower end 232 of the stem shaft 230 (in other words a core distal end of the stem core 220). The stem core 220 with the two stem dampers 252, 254 may be assembled into the stem sleeve 210.

The shock absorber system 250 may provide the hip prosthesis device 200 the intrinsic ability for resisted telescoping/displacement both in loading conditions as well as off-loading conditions. This may be achieved by the shock absorber system 250, assembled within the stem sleeve 210 of the hip prosthesis device 200. The shock absorber system 250, that is, e.g., the stem dampers 252, 254 and/or a spring system and/or a damping system, may be hydraulic, compression or hysteresis of structural material such as springs, pneumatic, dry friction or solid state, tapered chain shock absorbers, or any combination thereof. The maximum displacement allowed may range from 0-30 mm. However, for practical purposes, the maximum displacement should be in the range of 2-5 mm during normal loading conditions.

The femoral stem 202 may further include a closure cap 260 (in other words a stem cap) positioned so as to close the hole opening 216 and having a through hole 262 provided therethrough, through which the neck 240 extends with its lower neck portion 242. The closure cap 260 may prevent fluid from entering the stem sleeve 210. In other words, the stem sleeve 210 may be closed off with the closure cap 260. The femoral stem 202 may further include an optional stem gasket/membrane for sealing off the stem core 220 from the external environment.

Embodiments of the hip prosthesis device 200 may be used to replace a hip joint of a patient. The femoral head 201 attached to the upper neck portion 244 of the stem core 220 may be received in a generally hemispherical cup attached to an acetabulum of the patient such that the hip prosthesis device 200 may articulate freely within the generally hemispherical cup. The femoral stem 202 of the hip prosthesis device 200 may be secured within a femur by use of appropriate bone cement, or biological fixation.

Figure 2C:
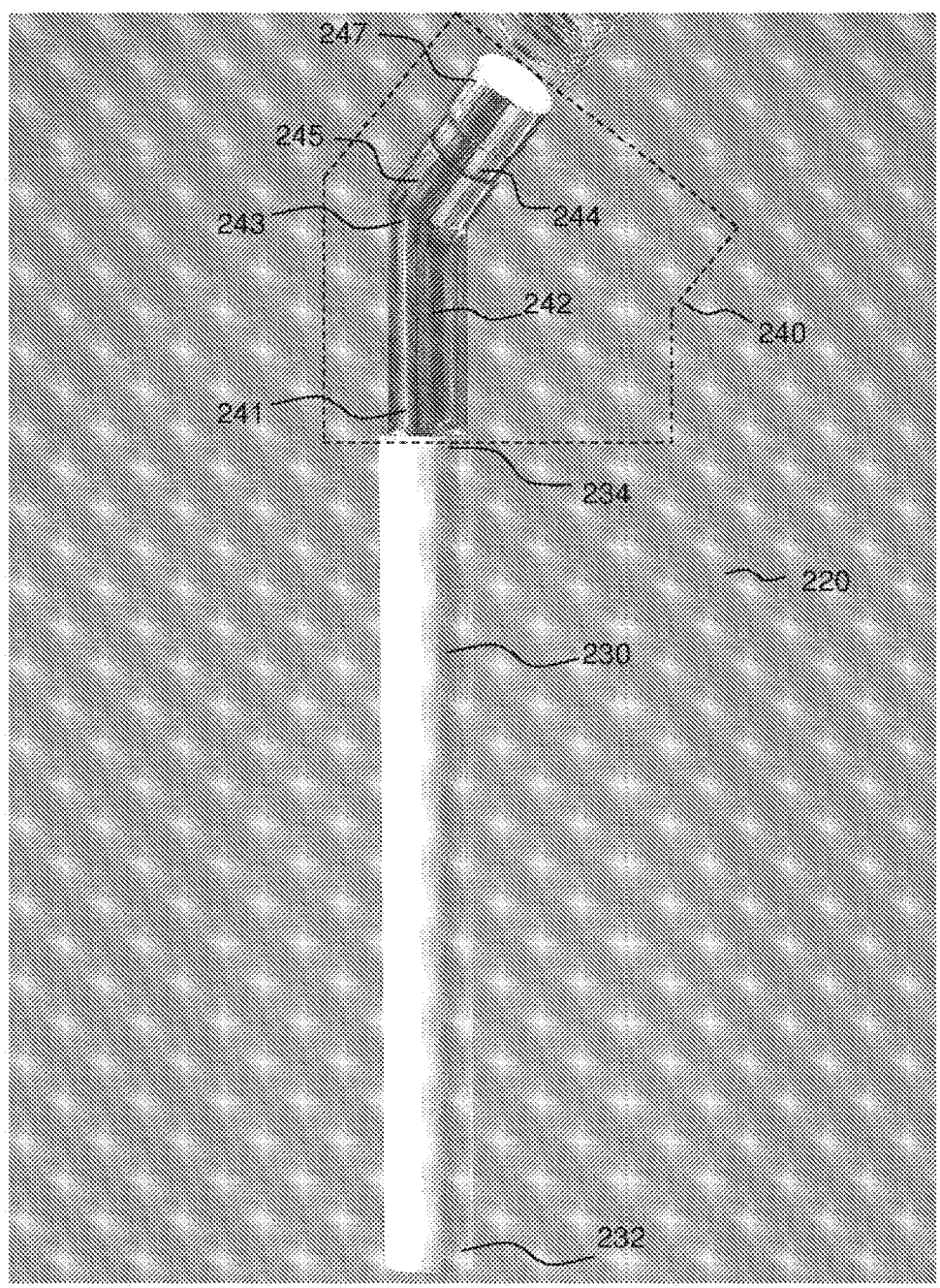
FIG. 2C shows a closed up view of a stem core of a femoral stem of the hip prosthesis device of FIG. 2A according to various embodiments.

FIG. 2C shows a closed up view of the stem core 220 of the femoral stem 202 of the hip prosthesis device 200. The stem core 220 may be a single continuous component that may be fabricated via standard machining techniques from material monoblock or casted or 3-D printed from raw material powder or beads. The stem core 220 may be surface coated with a resistant material for better wear characteristics. The stem core 220 may include a neck 240 subdivided into upper neck portion 244 and lower neck portion 242. The stem core 220 may further include a stem shaft 230 (in other words a core shaft). The stem shaft 230 may include a lower end 232 (in other words a core distal end).

Both the upper neck portion 244 and lower neck 242 may be circular in cross-section with a uniform diameter. The diameter of the upper neck portion 244 and lower neck 242 may be smaller than diameter of the stem shaft 230.

Figure 2D:
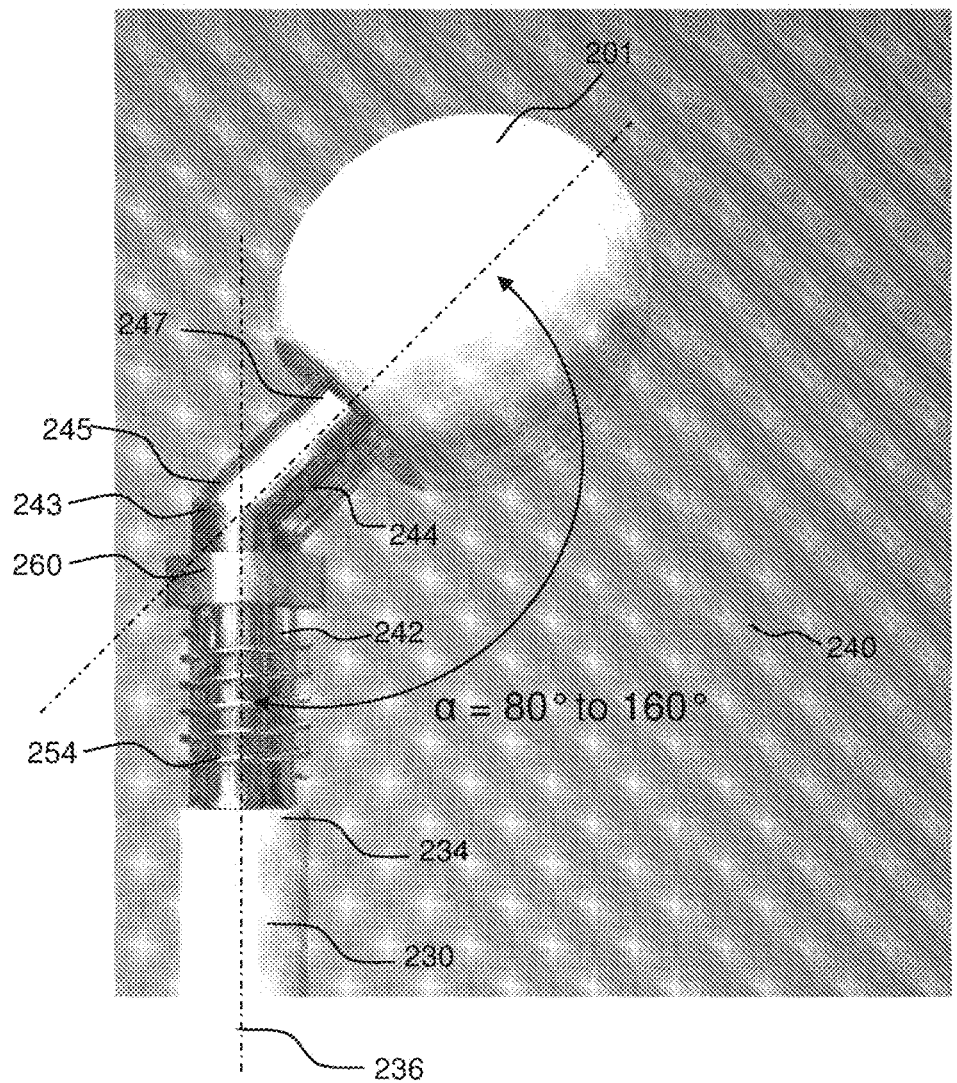
FIG. 2D shows a closed up view of a neck of the femoral stem of the hip prosthesis device of FIG. 2A according to various embodiments.

FIG. 2D shows a closed up view of the neck 240 of the femoral 202 of the hip prosthesis device 200. The upper neck portion 244 may be angled between 80 and 160 degrees from the axial axis (or the longitudinal axis) 236 of the stem shaft 230 of the stem core 220. The lower neck portion 242 may be connected to the stem shaft 230 along the axial axis 214 of the stem shaft 230. Thus, the upper neck portion 244 and the lower neck portion 242 may be angled relative to each other. The upper neck portion 244 may be adapted for the attachment of a generally spherical head 201. The lower neck portion 242 may be adapted for the accommodation of a proximal stem damper 254 of the shock absorber mechanism 250.

The stem shaft 230 may be circular in cross-section with a uniform diameter. The geometry of the stem shaft 230 may be adapted for the stem core 220 axial telescoping action within the blind hole (in other words the internal cavity) 212 of the stem sleeve 210. The stem shaft 230 may be rotatably arranged in the blind hole 212 so as to be rotatable about the longitudinal axis 236 of the stem shaft 230. An outer diameter of the stem shaft 230 and an inner diameter of the blind hole 212 may be provided so as to provide a running fit between the stem shaft 230 and the blind hole 212. The stem shaft 230 may be adapted to longitudinally slide in the blind hole 212 relative to the stem sleeve 210 in a gliding manner. In other words, the stem shaft 230 may move in an axial telescoping motion relative to the blind hole 212 of the stem sleeve 210. The articulating surfaces for the axial telescoping motion may be coated with a resistant material. In other words, a surface of the stem shaft 230 or a surface of the stem core 220 may be coated with a resistant material for better wear characteristics. An inner surface of the blind hole 212 of the stem sleeve 210 may also be coated with a resistant material.

According to various embodiments, where rotation between the stem core 220 and the stem sleeve 210 may be required to be limited, a triangular cross sectional stem core 220 and a triangular cross sectional stem shaft 230 may be adopted. According to various embodiments, the cross sectional shape of the stem core 220 in relation to the stem sleeve 210 may include various different shapes. In other words, the blind hole 212 and the stem shaft 230 may have non-circular cross sections so as to allow only a limited rotation of the stem shaft 230 in the blind hole about the longitudinal axis 236 of the stem shaft 230 relative to the stem sleeve 210.

The lower end 232 of the stem shaft 230 (in other words the core distal end) may be circular in cross-section with a uniform diameter. The lower end 232 of the stem shaft 230 may be configured for accommodation of a distal stem damper 252 of the shock absorber mechanism 250.

The stem core 220 may be made from dense and strong material to resist the structural loading during activities that required hip function. The surface characteristics of the stem shaft 230 may be hard wearing and of low friction so as to minimize wear during axial telescoping motion. Such surface characteristics may be achieved via polishing or surface coated. According to various embodiments, the stem shaft 230 may be provided with an outer coating which is of higher wear resistance in comparison to a coated surface of the stem shaft 230, which coated surface is provided with the outer coating.

Figure 2E:
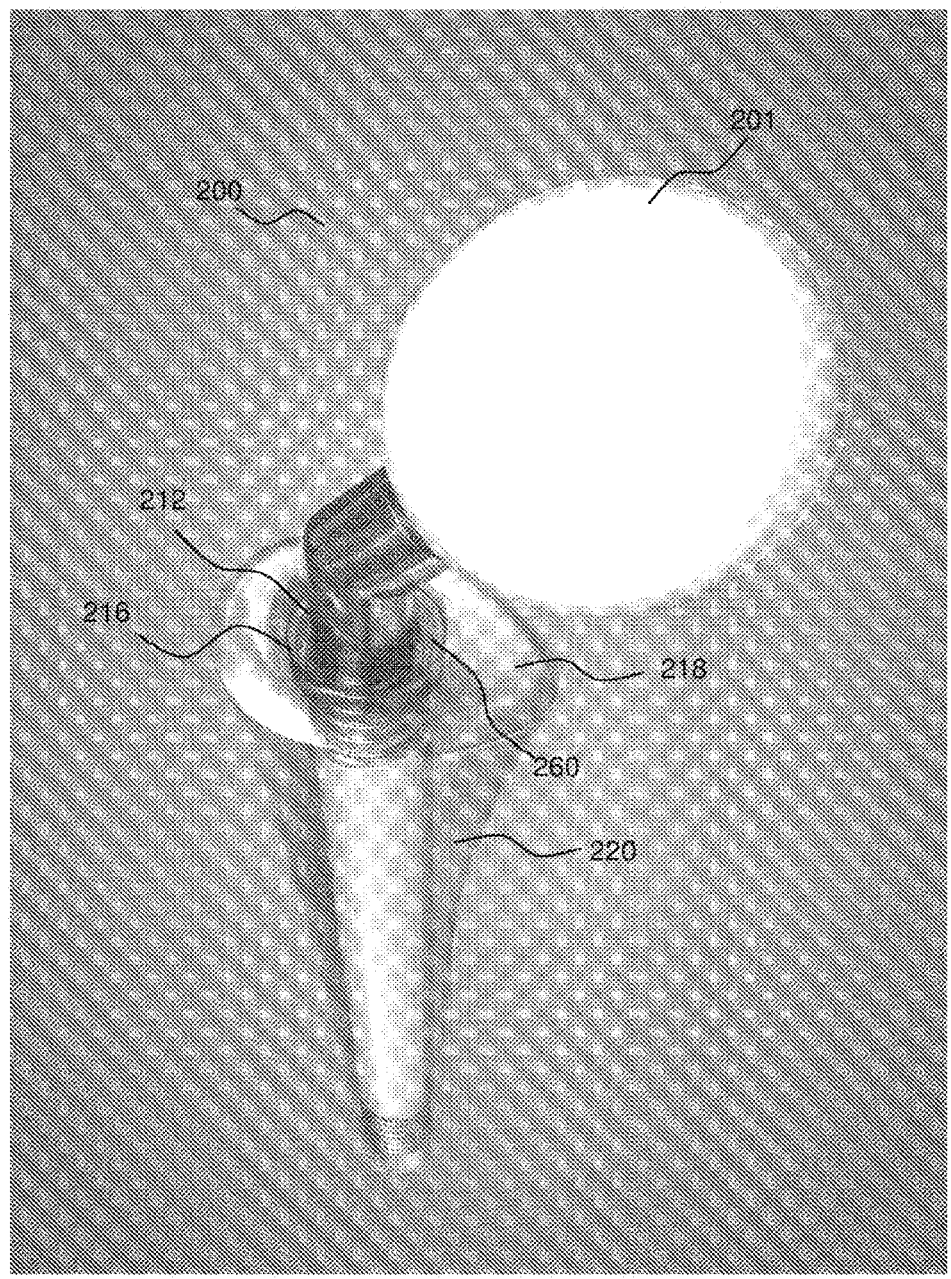
FIG. 2E shows a closed up top angled view of the hip prosthesis device of FIG. 2A according to various embodiments.
Figure 2F:
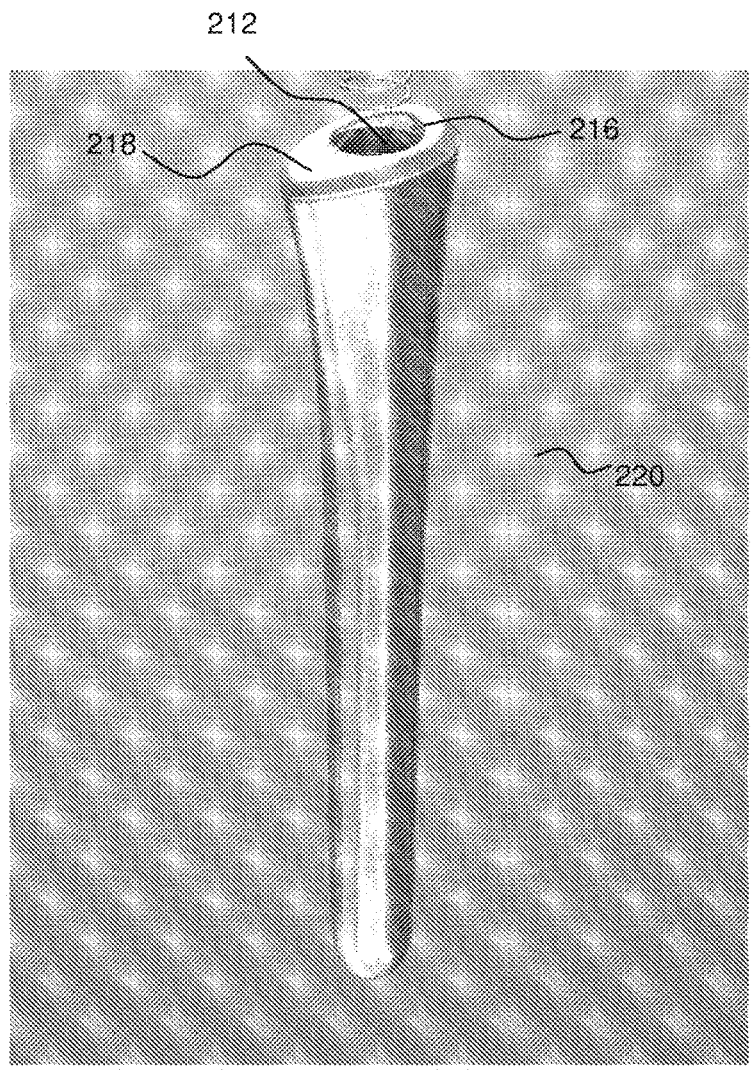
FIG. 2F shows a closed up view of a stem sleeve of the femoral stem of the hip prosthesis device of FIG. 2A according to various embodiments.

FIG. 2E shows a closed up top angled view of the hip prosthesis device 200. FIG. 2F shows a closed up view of the stem sleeve 210 of the femoral stem 202 of the hip prosthesis device 200. As shown, the stem sleeve 210 may include the blind hole 216 (in other words the internal cavity) that may be circular in cross-section with a uniform diameter. The geometry of the blind hole 216 may be adapted to accommodate stem shaft 220 as well as the distal stem damper 252 of the shock absorber mechanism 250. The external geometry of the stem sleeve 210 at the proximal end (in other words the upper frontal end) 218 may include a calcar collar to facilitate load transfer.

The blind hole 212 may have a hole opening 216 at the proximal end (in other words the upper frontal end) 218 of the stem sleeve 210. Internal threadings may be cut in the hole opening 216 to facilitate locking of the closure cap (in other words stem cap) 260. According to various embodiments, the hole opening 216 may be provided with an inner thread and the closure cap 260 may be provided with a corresponding outer thread. The closure cap 260 may be locked into the hole opening 216 by screwing the closure cap 260 into the hole opening 216.

The surface characteristics of the blind hole 212 are hard wearing and of low friction so as to minimize wear during axial telescoping motion. The surface characteristics on the external surface of the stem sleeve 210 may be polished or surface coated. The stem sleeve 210 may be fixed with cement or biologically (bony ingrowth or ongrowth). The stem sleeve 210 may be made from dense and strong material to resist structural loading during activities that required hip function. The geometry of the stem sleeve 210 may include but may not be limited to tapered or intra medullary canal form filling. The stem sleeve 210 may include a calcar collar.

According to various embodiments the shock absorber mechanism 250 of the femoral stem 202 of the hip prosthesis device 200 may be operatively provided between the stem shaft 230 and the stem sleeve 210 so as to act against a downwardly directed as well as against an upwardly directed longitudinal sliding motion of the stem shaft relative to the stem sleeve. The shock absorber mechanism 250 may be provided as a spring mechanism, or as a damping mechanism, or as a spring and damping mechanism.

As shown in FIGS. 2A and 2B, the shock absorber mechanism 250 may include a first spring device (in other words a distal stem damper) 252, or a first spring device 252 and a second spring device (in other words a proximal stem damper) 254. The first spring device 252 and the second spring device 254 may be configured for impact force absorption during load bearing or motion activities that required the hip function. The arrangement of the first spring device 252 and the second spring device 254 may be such that during load application, the first spring device 252 may be compressed to absorb the impact force while the second spring device 254 may be extended. During unloading, the energy is released causing both the first spring device 252 and the second spring device 254 to return to their original length due to spring-like effect and this in turn provide the telescopic axial action for stem core 220. The maximum extension for both the first spring device 252 and the second spring device 254 may be between the range of 0 to 30 mm, and preferably between the range of 0 to 5 mm during normal conditions.

The means to achieve the impact force absorption may include helical springs and/or a volumetric spring, such as a non-crosslinked paste-like material or similar.

According to various embodiments, the first spring device 252 of the shock absorber mechanism 250 may be arranged between a lower end 232 of the stem shaft 230 and a bottom of the blind hole 212. The second spring device 254 may be arranged between the upper end 234 of the stem shaft 230 and the closure cap 260.

According to various embodiments the first spring device 252 may include a first helical spring. A first longitudinal end of the first helical spring may abut against the lower end 232 of the stem shaft 230 and an opposite second longitudinal end of the first helical spring may abut against the bottom of the blind hole 212.

According to various embodiments, the second spring device 254 may include a second helical spring. A first longitudinal end of the second helical spring may abut against the upper end 234 of the stem shaft 230 and an opposite second longitudinal end of the second helical spring may abut against the closure cap 260.

According to various embodiments, the second helical spring may be arranged on the lower neck portion 242. In this arrangement, an outer diameter of both the upper neck portion 244 and the lower neck portion 242 may be smaller than an outer diameter of the stem shaft 230. An inner diameter of the through hole 262 of the closure cap 260 may be smaller than the outer diameter of the stem shaft 230. Further, an inner diameter of the second helical spring may be smaller than the outer diameter of the stem shaft 230 and an outer diameter of the second helical spring may be larger than an inner diameter of the through hole 262 of the closure cap 260.

According to various embodiments, the primary function of the closure cap (in other words the stem cap) 260 may be to act as a retainer to prevent the second spring device 254 as well as the stem core 220 from being ejected from the stem sleeve 210 during unloading. The secondary function of the closure cap 260 may be to prevent fluid from entering into the blind hole (in other words the internal cavity) 212 of the stem sleeve 210 and also to prevent any wear particles resulted from the axial telescoping motion from exiting the blind hole 212 of the stem sleeve 210. A flexible, impermeable and inert membrane may also be provided to connect the closure cap 260 to the neck 240 of the stem core 220 so as to facilitate the secondary function. The closure cap 260 may be threaded externally and screwed into the internal threads on the blind hole 212 of the stem sleeve 210. According to various embodiments, the closure cap 260 may also be welded in the hole opening 216 of the blind hole 212. The closure cap 260 may close the hole opening 216 of the blind hole 212. The lower neck portion 242 of the neck 240 may extend through the through hole 262 of the closure cap 260. The closure cap 260 may be adapted to be in a sliding and sealed engagement with the lower neck portion 242 extending therethrough. The closure cap 260 may be made from dense and strong material to resist the impact forces.

According to various embodiments, the femoral head 201 may be generally spherical in geometry. The femoral head 201 may be attached to the stem core 220 at the neck 240 via the upper neck portion 244. An internal cavity of the femoral head 201 with geometry corresponding to the upper end 247 of the upper neck portion 244 may facilitate attaching the femoral head 201 to the upper neck portion 244. The femoral head 201 may be made from dense, strong, low wearing and low friction material such as highly polished metal or ceramic so as to allow it to freely articulate within a generally hemispherical cup.

According to various embodiments, a stem gasket/membrane may optionally be attached above and over the closure cap 260 to help prevent fluid from entering into blind hole 212 of the stem sleeve 210 and also to prevent any wear particles due to the axial telescoping motion from exiting the blind hole 212. The material for the stem gasket may be any suitable biocompatible material such as silicon rubber etc.

According to various embodiments, the hip prosthesis device 100, 200 (in other words the orthopedic hip stem implant) may represent an improvement over other existing devices as discussed in the background section and provides the advantage of true shock absorption with the ability to return to its original position facilitated by the shock absorber mechanism 150, 250 of the hip prosthesis device 100, 200 during both joint force loading and unloading. Embodiments of the hip prosthesis device 100, 200 may minimise the problems highlighted in the background section by dissipating some of the kinetic energy by hysteresis in the shock absorber mechanism 150, 250 (in other words the spring and/or damping system). The telescoping motion of the hip prosthesis device 100, 200 may be resisted and controlled in magnitude, both in the loading and unloading phase. In addition, the cylindrical stem core 120, 220 may be able to rotate with respect to the fixed stem sleeve 110, 210. This may allow the hip prosthesis device 100, 200 to maintain an ideal neck to shaft angle, or orientation or version in relation to the acetabular prosthesis. This may reduce the risk of dislocation and loosening caused by rotational stress. Limitation of the rotation of the stem core 120, 220 and stem sleeve 110, 210 may also be achieved in specific circumstances, for example, by having a stem core 120, 220 with a triangular cross section fitted into a triangular blind hole 212 of the stem sleeve 110, 210 (in other words a triangular sleeve slot).

Embodiments of the hip prosthesis device 100, 200 may provide a modular femoral stem implant for total or partial hip replacement that may absorb impact force and dissipate kinetic energy during loading. The femoral stem assembly 102, 202 may include a stem core 120, 220, a shock absorber mechanism 150, 250 within a sleeve 110, 210. The shock absorber mechanism 150, 250 may include one spring device 252 (in other words damping system) or two spring devices 252, 254 (in other words two damping systems) within the femoral stem 102, 202. During unloading of the hip joint, the stem core 120, 220 and the shock absorber mechanism 150, 250, including stem spring and/or damping mechanism, may be prevented from ejecting out of the stem sleeve 210 via the use of a screwed-on or welded closure cap (in other words stem cap) 260. The low friction, hard wearing surfaces of the blind hole 212 of the stem sleeve 210 and the stem shaft 230 together with the shock absorber mechanism 150, 250 may allow the stem core 220 to be capable for axial telescoping motion independent of the stem sleeve 210 after implantation in the femur. The stem core 220, which may be cylindrical, may also rotate within the stem sleeve 210, allowing an optimal orientation or version of the neck angle in relation to the acetabular which may optimize the internal and external rotation of the hip.

Embodiments of the hip prosthesis device 100, 200 may provide resisted and controlled magnitude telescoping within the femoral stem 102, 202. This telescoping may be achieved with the shock absorber mechanism 150, 250 (in other words the spring and/or damping mechanism) within the stem sleeve 210 of the hip prosthesis device 100, 200. This shock absorber mechanism 150, 250 may result in resisted telescoping on axial loading, with or without resisted telescoping on off-loading of the hip prosthesis device 100, 200, for example, using the first spring device 252. The first spring device 252 may allow dissipation of mechanical energy and reduces wear and loosening of the hip prosthesis device 100, 200. The hip prosthesis device 100, 200 may also allow controlled rotation of the neck 140, 240 of the femoral stem 102, 202 in relation to the stem sleeve 110, 210, thus allowing a variable neck stem angle to allow the ideal orientation or version to the acetabular throughout the hip's anatomical range of motion, thus increasing range of motion and preventing dislocations.

Embodiments of the hip prosthesis device 100, 200 may reduce or dissipate overall mechanical energy transferred to the bone-cement or bone-prosthesis interface as well as the articulating surface. Embodiments of the hip prosthesis device 100, 200 may reduce peak impact forces on the bone-cement or bone-prosthesis interface as well as the articulating surface during loading/off-loading. Embodiments of the hip prosthesis device 100, 200 may mimic the anatomical displacement by the cartilage/labrum compression seen in the healthy hip, during axial loading conditions on weight bearing. Embodiments of the hip prosthesis device 100, 200 may result in a viable and ideal stem shaft 130, 230 to neck 140, 240 angle, and an orientation or version in relation to the native acetabular or acetabular prosthesis during internal and external rotation of the hip.

Embodiments of the hip prosthesis device 100, 200 may result in a reduced loosening of the hip prosthesis device 100, 200. Embodiments of the hip prosthesis device 100, 200 may result in a reduced risk of peri prosthetic fractures and thigh pain caused by high femoral stress due to the difference in the Young's modulus between the femoral shaft/bone and the prosthesis femoral stem 102, 202. Embodiments of the hip prosthesis device 100, 200 may result in minimize wear/fracture in the articulating surfaces. Embodiments of the hip prosthesis device 100, 200 may also reduce peak forces in the intevetebral disc and facet joints in the spine. Embodiments of the hip prosthesis device 100, 200 may also reduce peak forces in distal joints (knee, ankle and foot). Embodiments of the hip prosthesis device 100, 200 may also reduce rotational stress on the hip prosthesis device 100, 200 and reduce dislocations caused by too much anteversion or retroversion of the hip prosthesis device 100, 200 in relation to the acetabular (native or prosthesis). This may result in an increased range of motion in terms of internal and external rotation of the hip. Embodiments of the hip prosthesis device 100, 200 may also reduce the risk of fracture of the articular surfaces especially in hard materials like ceramic.

Embodiments of the hip prosthesis device 100, 200 may prolong the survival or lifespan of the hip prosthesis device 100, 200, reduce complications and reduce revision rates especially in high functional demand patients. The placement of the shock absorber mechanism 150, 250 (in other words the spring and/or damping mechanism) within the femoral stem 102, 202 instead of the cup may allows the hip prosthesis device 100, 200 to be used in hemiarthroplasty. The placement of the shock absorber mechanism 150, 250 within the femoral stem 102, 202 may also avoid having the shock absorber mechanism 150, 250 within the neck 140, 240 where space or volume is limited, and weakening of the moving parts of a shock absorber mechanism at the neck may cause failure of the hip prosthesis device. The stem sleeve 110, 210 may ensure that there is minimal movement between bone and cement, or bone and prosthesis interface. Embodiments of the hip prosthesis device 100, 200 may also allow certain amounts of flexibility and/or damping at varying degrees of flexion and extension of the hip joint.

Various embodiments are defined by the following examples.

Example 1 is a hip prosthesis device comprising a femoral stem which is provided to be implanted within a femoral bone, the femoral stem comprising:

an elongate stem sleeve having a blind hole formed therein and extending in a longitudinal direction thereof and having a hole opening at an upper frontal end of the stem sleeve;

a stem core which has an elongate stem shaft inserted in the blind hole and arranged therein so as to be slidable in longitudinal direction thereof, a neck with a lower neck portion which is fixedly attached, with a lower end thereof, to an upper end of the stem core, and with an upper neck portion which is fixedly attached, with a lower end thereof, to an upper end of the lower neck portion and which has an upper end, to which a femoral head is attachable;

a shock absorber mechanism arranged within the stem sleeve and operatively provided between the stem shaft and the stem sleeve so as to act at least against a downwardly directed longitudinal sliding motion of the stem shaft relative to the stem sleeve; and a closure cap positioned so as to close the hole opening and having a through hole provided therethrough, through which the neck extends with its lower neck portion.

In Example 2, the subject matter of example 1 may further include that the shock absorber mechanism is operatively provided between the stem shaft and the stem sleeve so as to act against a downwardly directed as well as optionally against an upwardly directed longitudinal sliding motion of the stem shaft relative to the stem sleeve.

In Example 3, the subject matter of example 1 and 2 may further include that the shock absorber mechanism is provided as a spring mechanism, or as a damping mechanism, or as a spring and damping mechanism.

In Example 4, the subject matter of anyone of examples 1 to 3 may further include that the shock absorber mechanism comprises a first spring device arranged between a lower end of the stem shaft and a bottom of the blind hole, and a second optional spring device arranged between the upper end of the stem shaft and the closure cap.

In Example 5, the subject matter of example 4 may further include that the first spring device comprises a first helical spring, a first longitudinal end of which abuts against the lower end of the stem shaft and an opposite second longitudinal end of which abuts against the bottom of the blind hole, and wherein the second optional spring device comprises a second helical spring, a first longitudinal end of which abuts against the upper end of the stem shaft and an opposite second longitudinal end of which abuts against the closure cap.

In Example 6, the subject matter of example 5 may further include that the second helical spring is arranged on the lower neck portion.

In Example 7, the subject matter of anyone of examples 1 to 6 may further include that the hole opening is provided with an inner thread and the closure cap is provided with a corresponding outer thread and is screwed into the opening.

In Example 8, the subject matter of anyone of examples 1 to 7 may further include that the closure cap closes the hole opening in a sealed manner, wherein the closure cap is in a sliding and scaled engagement with the lower neck portion extending therethrough.

In Example 9, the subject matter of anyone of examples 1 to 8 may further include an artificial spherical femoral head which is fixedly attached to the upper end of the upper neck portion.

In Example 10, the subject matter of anyone of examples 1 to 9 may further include that the stem shaft is rotatably arranged in the blind hole so as to be rotatable about its longitudinal axis.

In Example 11, the subject matter of example 10 may further include that the blind hole and the stem shaft have circular cross sections, or wherein the blind hole and the stem core have non-circular cross sections so as to allow only a limited rotation of the stem core in the blind hole about its longitudinal direction relative to the stem sleeve.

In Example 12, the subject matter of anyone of examples 1 to 11 may further include that the stem shaft is provided with an outer coating which is of higher wear resistance in comparison to a coated surface of the stem shaft, which coated surface is provided with the outer coating.

In Example 13, the subject matter of anyone of examples 1 to 12 may further include that an outer diameter of the stem shaft and an inner diameter of the blind hole are provided so as to provide a running fit between stem shaft and blind hole.

In Example 14, the subject matter of anyone of examples 1 to 13 may further include that the stem shaft can longitudinally slide in the blind hole relative to the stem sleeve in a gliding manner.

In Example 15, the subject matter of anyone of examples 1 to 14 may further include that the upper neck portion and the lower portion are angled relative to each other.

In Example 16, the subject matter of anyone of examples 1 to 15 may further include that an outer diameter of both the upper neck portion and the lower neck portion is smaller than an outer diameter of the stem shaft, and wherein an inner diameter of the through hole of the closure cap is smaller than the outer diameter of the stem shaft.

In Example 17, the subject matter of anyone of examples 1 to 16, insofar as combined with examples 6 and 16, may further include that an inner diameter of the first helical spring is smaller than the outer diameter of the stem shaft and an outer diameter of the helical spring is larger than an inner diameter of the through hole of the closure cap.

While the invention has been particularly shown and described with reference to specific embodiments, it should be understood by those skilled in the art that various changes in form and detail may be made therein without departing from the scope of the invention as defined by the appended claims. The scope of the invention is thus indicated by the appended claims and all changes which come within the meaning and range of equivalency of the claims are therefore intended to be embraced.

The invention claimed is:

1. A hip prosthesis device comprising a femoral stem which is provided to be implanted within a femoral bone, the femoral stem comprising:
   an elongate stem sleeve having a blind hole formed in the elongate stem sleeve, the blind hole extending in a longitudinal direction of the elongate stem sleeve and having a hole opening at an upper frontal end of the elongate stem sleeve;
   a stem core which has
      an elongate stem shaft inserted in the blind hole and arranged therein so as to be slidable in the longitudinal direction of the elongate stem sleeve,
      a neck with
         a lower neck portion which is fixedly attached, with a lower end thereof, to an upper end of the stem shaft, and with
         an upper neck portion which is fixedly attached, with a lower end thereof, to an upper end of the lower neck portion and which has an upper end, to which a femoral head is attachable;
   a shock absorber mechanism arranged within the elongate stem sleeve and operatively provided between the stem shaft and the elongate stem sleeve so as to act at least against a downwardly directed longitudinal sliding motion of the stem shaft relative to the elongate stem sleeve in the longitudinal direction of the elongate stem sleeve;
   and
   a closure cap positioned so as to close the hole opening and having a through hole provided therethrough, wherein the lower neck portion of the neck extends through the through hole of the closure cap,
   wherein the upper neck portion and the lower neck portion are angled relative to each other.

2. The hip prosthesis device according claim 1, wherein the shock absorber mechanism is operatively provided between the stem shaft and the elongate stem sleeve so as to act against a downwardly directed as well as against an upwardly directed longitudinal sliding motion of the stem shaft relative to the elongate stem sleeve.

3. The hip prosthesis device according to claim 1, wherein the shock absorber mechanism is provided as a spring mechanism, or as a damping mechanism, or as a spring and damping mechanism.

4. The hip prosthesis device according to claim 1, wherein the shock absorber mechanism comprises
   a first spring device arranged between a lower end of the stem shaft and a bottom of the blind hole.

5. The hip prosthesis device according to claim 4, wherein the shock absorber mechanism comprises
   a second spring device arranged between the upper end of the stem shaft and the closure cap.

6. The hip prosthesis device according to claim 5, wherein the second spring device comprises a second helical spring, a first longitudinal end of which abuts against the upper end of the stem shaft and an opposite second longitudinal end of which abuts against the closure cap, and wherein the second helical spring is arranged on the lower neck portion.

7. The hip prosthesis device according to claim 6, wherein an outer diameter of both the upper neck portion and the lower neck portion is smaller than an outer diameter of the stem shaft, and wherein an inner diameter of the through hole of the closure cap is smaller than the outer diameter of the stem shaft.

8. The hip prosthesis device according to claim 7, wherein an inner diameter of the second helical spring is smaller than the outer diameter of the stem shaft and an outer diameter of the second helical spring is larger than an inner diameter of the through hole of the closure cap.

9. The hip prosthesis device according to claim 4, wherein the first spring device comprises a first helical spring, a first longitudinal end of which abuts against the lower end of the stem shaft and an opposite second longitudinal end of which abuts against the bottom of the blind hole.

10. The hip prosthesis device according to claim 1, wherein the stem shaft is rotatably arranged in the blind hole so as to be rotatable about a longitudinal axis of the stem shaft.

11. The hip prosthesis device according to claim 10, wherein the blind hole and the stem shaft have circular cross sections.

12. The hip prosthesis device according to claim 10, wherein the blind hole and the stem shaft have non-circular cross sections so as to allow only a limited rotation of the stem shaft in the blind hole about the longitudinal axis of the stem shaft relative to the stem sleeve.

13. The hip prosthesis device according to claim 1, wherein the hole opening is provided with an inner thread and the closure cap is provided with a corresponding outer thread and is screwed into the hole opening.

14. The hip prosthesis device according to claim 1, wherein the closure cap closes the hole opening in a sealed manner, wherein the closure cap is in a sliding and sealed engagement with the lower neck portion extending therethrough.

15. The hip prosthesis device according to claim 1, further including the femoral head which is fixedly attached to the upper end of the upper neck portion, wherein the femoral head is an artificial spherical femoral head.

16. The hip prosthesis device according to claim 1, wherein the stem shaft is provided with an outer coating which is of higher wear resistance in comparison to a pre-coated surface of the stem shaft, which pre-coated surface is provided with the outer coating.

17. The hip prosthesis device according to claim 1, wherein an outer diameter of the stem shaft and an inner diameter of the blind hole are provided so as to provide a running fit between stem shaft and blind hole.

18. The hip prosthesis device according to claim 1, wherein the stem shaft is adapted to slide longitudinally in the blind hole relative to the elongate stem sleeve in a gliding manner.

* * * * *